US007998690B2

(12) United States Patent
Liang et al.

(10) Patent No.: US 7,998,690 B2
(45) Date of Patent: Aug. 16, 2011

(54) METHODS FOR THE DETECTION AND MONITORING OF CONGESTIVE HEART FAILURE

(75) Inventors: Bruce Tsan-Tang Liang, Avon, CT (US); W. David Hager, Bloomfield, CT (US)

(73) Assignee: The University of Connecticut, Farmington, CT (US)

( * ) Notice: Subject to any disclaimer, the term of this patent is extended or adjusted under 35 U.S.C. 154(b) by 0 days.

(21) Appl. No.: 12/765,351

(22) Filed: Apr. 22, 2010

(65) Prior Publication Data

US 2010/0203566 A1 Aug. 12, 2010

Related U.S. Application Data

(62) Division of application No. 12/400,061, filed on Mar. 9, 2009, now Pat. No. 7,745,150.

(60) Provisional application No. 61/034,698, filed on Mar. 7, 2008.

(51) Int. Cl.
*G01N 33/53* (2006.01)
(52) U.S. Cl. ............................ 435/7.1; 435/7.2; 436/518
(58) Field of Classification Search ........................ None
See application file for complete search history.

(56) References Cited

U.S. PATENT DOCUMENTS

| 5,485,277 | A | 1/1996 | Foster |
| 5,492,840 | A | 2/1996 | Malmqvist et al. |
| 5,567,301 | A | 10/1996 | Stetter et al. |
| 2002/0155579 | A1 | 10/2002 | Krebs et al. |

OTHER PUBLICATIONS

American Heart Association; "Heart Disease and Stroke Statistics—2006 Update"; Dallas, TX; 43 pages; (2006).
Bing; "Hypothesis: Apoptosis May be a Mechanism for the Transition to Heart Failure with Chronic Pressure Overload"; J. Mol. Cell Cardiol.; 26; pp. 943-948; (1994).
Budihardjo, et al.; "Biochemical Pathways of Caspase Activation During Apoptosis"; Annu. Rev. Cell Dev. Biol.; 15; pp. 269-290; (1999).
Bursi, et al.; "Systolic and Diastolic Heart Failure in the Community"; JAMA; 296; pp. 2209-2216; (2006).
Buvat De Virginy; "Novel and Potential Future Biomarkers for Assessment of the Severity and Prognosis of Chronic Heart Failure"; Heart Fail Rev. 11; pp. 333-344; (2006).
Capasso, et al.; "Left Ventricular Failure Induced by Long-Term Hypertension in Rats"; Circ. Res.; 66; pp. 1400-1412; (1990).
Caspase-3 Antibody; Cell Signaling Technology product insert #9662. Rev. Oct. 2005.; 2 pages.
Cleaved Caspase-3 (Asp175) Antibody; Cell Signaling Technology product insert #9661. Rev. Nov. 2006; 3 pages.
Engelmann, et al.; "Morphometric Analysis of Cardiac Hypertrophy During Development, Maturation, and Senescence in Spontaneously Hypertensive Rats"; Circ. Res.; 60; pp. 487-494; (1987).

Gottlieb, et al.; "Reperfusion Injury Induces Apoptosis in Rabbit Cardiomyocytes"; Journal of Clinical Investigation; 94; pp. 1621-1628; (1994).
Hunt; "ACC/AHA 2005 Guideline Update for the Diagnosis and Management of Chronic Heart Failure in the Adult"; J. Am. Coll. Cardiol.; 46; pp. 1-82; (2005).
Itoh, et al.; "DNA Fragmentation of Human Infarcted Myocardial Cells Demonstrated by the Nick End Labeling Method and DNA Agarose Gel Electrophoresis"; American Journal of Pathology; 146; pp. 1325-1331; (1995).
Kinnunen, et al.; "Mechanisms of Atrial and Brain Natriuretic Peptide Release from Rat Ventricular Myocardium: Effect of Stretching"; Endocrinology; 132; pp. 1961-1970; (1993).
Kostin, et al.; "Myocytes Die by Multiple Mechanisms in Failing Human Hearts"; Circ. Res.; 92; pp. 715-724; (2003).
Massie; "Evolving Trends in the Epdemiologic Factors of Heart Failure: Ratonale for Preventve Strategies and Comprehensive Disease Management"; American Heart Journal; 133; pp. 703-712; (1997).
Mehra, et al.; "Obesity and Suppressed B-Type Natriuretic Peptide Levels in Heart Failure"; J Am Coll Cardiol.; 43; pp. 1590-1595; (2004).
Narula, et al.; "Apoptosis in Myocytes in End-Stage Heart Failure"; N Engl J Med.; 335; pp. 1182-1189; (1996).
Olivetti, et al.; "Acute Myocardial Infarction in Humans is Associated with Activation of Programmed Myocyte Cell Death in the Surviving Portion of the Heart"; J Mol Cell Cardiol.; 28; pp. 2005-2016; (1996).
Olivetti, et al.; "Apoptosis in the Failing Human Heart"; N Engl J Med.; 336; pp. 1131-1141; (1997).
PathScan Cleaved Caspase-3 (Asp175) Sandwich ELISA Kit. Cell Signaling Technology produce insert #7190. Rev. Dec. 2003; 6 pages.
Yasue, et al.; "Localization and Mechanism of Secretion of B-type Natriuretic Peptide in Comparison With Those of A-type Natriuretic Peptide in Normal Subjects and Patients with Heart Failure"; Circulation; 90; pp. 195-203; (1994).
Yoshimura, et al.; "Different Secretion Patterns of Atrial Natriuretic Peptide and Brain Natriuretic Peptide in Patients with Congestive Heart Failure"; Circulation; 87; pp. 464-469; (1993).
Wang, et al.; "Impact of Obesity on Plasma Natriuretic Peptide Levels"; Circulation; 109; pp. 594-600; (2004).
Yturralde, et al.; "Diagnostic Criteria for Diastolic Heart Failure"; Prog in Cardiovas Dis.; 47; pp. 314-319; (2005).
"Cardiac Function and Heart Failure"; Journal of the American College of Cardiology, Elservier, New York, NY, US, vol. 51, No. 10, pp. A35-A82, XP022511990 (2008).
Wang et al.; "P38 Mitogen Activated Protein Kinase Mediates Both Death Signaling and Functional Depression in the Heart"; The Annals of Thoracic Surgery; Elservier; 80; pp. 2235-2241; XP005174676; (2005).
Sharma, et al.: "Activation of Apoptotic Processes During Transition from Hypertrophy to Heart Failure in Guinea Pigs"; American Journal of Physiology, Heart and Circulatory Physiology; 293; pp. H1384-H1390; XP002555657; (2007).
International Search Report and Written Opinion; International Application No. PCT/US2009/036492; International Filing Date Mar. 9, 2009; Applicant's File Reference UCT0133PCT; Date of Mailing Nov. 30, 2009; 13 pages.

(Continued)

*Primary Examiner* — Jacob Cheu
(74) *Attorney, Agent, or Firm* — Cantor Colburn LLP (57) ABSTRACT

Disclosed herein are methods of detecting and/or prognosing congestive heart failure by detecting a proteolytic fragment of caspase-3 such as the p17 fragment or the p12 fragment. The congestive heart failure can be of any etiology, such as systolic or diastolic heart failure, ischemic or non-ischemic cardiomyopathy.

5 Claims, 3 Drawing Sheets

OTHER PUBLICATIONS

Todor et al. (Am J. Physiol. Heart Circ Physiol. 2002 vol. 283, p. H990-H995.
Sabbah et al. (Heart Failure Review 2000 vol. 5, p. 131-138.
Sharma et al. (Am J. Physiol. Heart Circ Physiol. 2007 vol. 293, p. H1384-H1390.
International Preliminary Report on Patentability; International Application No. PCT/US2009/036492; International Filing Date Mar. 9, 2009; 6 pages.
Sharma, et al.; "Activation of Apoptotic Process During Transition from Hypertrophy to Heart Failure in Guinea Pigs"; Am J Physiol Heart Circ Physiol; 293; pp. H1384-H1390; (2007).
Wang, et al.; "P38 Mitogen Activated Protein Kinase Mediates Both Death Signaling and Functional Depression in the Heart"; Ann Thorac Surg; 80; pp. 2235-2241; (2005).
ACC.Poster Contributions; Abstracts—Cardiac Function and Heart Failure; "Myocardial Function/Heart Failure—Basic Molecular"; presented Sunday, Mar. 30, 2008; McCormick Place, South Hall; p. A35-A82; (2008).

Fig. 1

Linearity of apoptotic HeLa cell lysates with $OD_{450}$

Patients with Heart Failure and Preserved EF Showed an Increase in the Caspase-3 P17 Level During Acute Decompensation

SEQUENCE LISTING

```
<160> NUMBER OF SEQ ID NOS: 3

<210> SEQ ID NO 1
<211> LENGTH: 277
<212> TYPE: PRT
<213> ORGANISM: Homo sapiens

<400> SEQUENCE: 1

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
```

```
                210                 215                 220
Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
                260                 265                 270

Leu Tyr Phe Tyr His
                275

<210> SEQ ID NO 2
<211> LENGTH: 147
<212> TYPE: PRT
<213> ORGANISM: Homo sapiens

<400> SEQUENCE: 2

Ser Gly Ile Ser Leu Asp Asn Ser Tyr Lys Met Asp Tyr Pro Glu Met
1               5                   10                  15

Gly Leu Cys Ile Ile Asn Asn Lys Asn Phe His Lys Ser Thr Gly
                20                  25                  30

Met Thr Ser Arg Ser Gly Thr Asp Val Asp Ala Ala Asn Leu Arg Glu
                35                  40                  45

Thr Phe Arg Asn Leu Lys Tyr Glu Val Arg Asn Lys Asn Asp Leu Thr
50                  55                  60

Arg Glu Glu Ile Val Glu Leu Met Arg Asp Val Ser Lys Glu Asp His
65                  70                  75                  80

Ser Lys Arg Ser Ser Phe Val Cys Val Leu Leu Ser His Gly Glu Glu
                85                  90                  95

Gly Ile Ile Phe Gly Thr Asn Gly Pro Val Asp Leu Lys Lys Ile Thr
                100                 105                 110

Asn Phe Phe Arg Gly Asp Arg Cys Arg Ser Leu Thr Gly Lys Pro Lys
                115                 120                 125

Leu Phe Ile Ile Gln Ala Cys Arg Gly Thr Glu Leu Asp Cys Gly Ile
                130                 135                 140

Glu Thr Asp
145

<210> SEQ ID NO 3
<211> LENGTH: 102
<212> TYPE: PRT
<213> ORGANISM: Homo sapiens

<400> SEQUENCE: 3

Ser Gly Val Asp Asp Asp Met Ala Cys His Lys Ile Pro Val Glu Ala
1               5                   10                  15

Asp Phe Leu Tyr Ala Tyr Ser Thr Ala Pro Gly Tyr Tyr Ser Trp Arg
                20                  25                  30

Asn Ser Lys Asp Gly Ser Trp Phe Ile Gln Ser Leu Cys Ala Met Leu
                35                  40                  45

Lys Gln Tyr Ala Asp Lys Leu Glu Phe Met His Ile Leu Thr Arg Val
                50                  55                  60

Asn Arg Lys Val Ala Thr Glu Phe Glu Ser Phe Ser Phe Asp Ala Thr
65                  70                  75                  80

Phe His Ala Lys Lys Gln Ile Pro Cys Ile Val Ser Met Leu Thr Lys
                85                  90                  95

Glu Leu Tyr Phe Tyr His
                100
```

METHODS FOR THE DETECTION AND MONITORING OF CONGESTIVE HEART FAILURE

CROSS-REFERENCE TO RELATED APPLICATIONS

This application is a divisional of Ser. No. 12/400,061 file Mar. 9, 2009, which claims the benefit of U.S. Patent Application Ser. No. 61/034,698 filed on Mar. 7, 2008, both of which are incorporated by reference herein in their entirety.

STATEMENT REGARDING FEDERALLY SPONSORED RESEARCH & DEVELOPMENT

This invention was made with support from the United States Government under Grant Number HL48225. The U.S. Government has certain rights in the invention.

BACKGROUND

Congestive heart failure (CHF) is divided into two types: chronic CHF and acute (or decompensated-chronic) CHF. Chronic CHF is a longer term, slowly progressive degenerative disease clinically categorized by the patient's ability to exercise or perform normal activities of daily living. CHF can be ischemic, heart muscle damage that results from coronary artery disease, such as heart attack, or non-ischemic, not related to coronary artery disease. CHF is further subdivided according to abnormalities in the cardiac cycle: namely, systolic heart failure (SHF) and diastolic heart failure (DHF). Both SHF and SHF have ventricular remodeling, but the characteristic difference is that in DHF there is not an increase in end diastolic volume, which describes the remodeling in SHF. While the left ventricle in SHF is dilated, compliant, and poorly contractile, the ventricle with DHF is small, stiff, and often hyperdynamic. With the arterial stiffening and hypertension which often accompany successful aging, the incidence of DHF is believed to account for 50% of the 4.6 million US citizens with congestive heart failure and of those hospitalized for congestion. The typical patient with DHF is quite different from the patient with SHF.

The identification of patients with CHF is done based on history and a physical examination during which the condition is often characterized by various signs and symptoms of intra-vascular and interstitial volume overload, including shortness of breath, irregular heart rate, abnormal heart rate and signs of edema. The use of biomarkers in evaluating heart failure may provide another way to identify patients. Brain natriuretic peptide or BNP is the most commonly used biomarker for diagnosing heart failure. It is released in response to ventricular stretch and is considered a marker for myocardial stress. While BNP is released primarily in the heart ventricles during hemodynamic overload, it is also released from brain, lungs, kidneys, and vascular tissues. It has been used most commonly in diagnosing systolic heart failure. Levels of BNP levels tend to be lower in diastolic heart failure, and its utility in assessing these patients is under evaluation.

There remains a need for new biomarkers suitable for the identification of biomarkers suitable for detecting and/or diagnosing congestive heart failure including systolic and diastolic heart failure, ischemic and non-ischemic heart failure.

SUMMARY

In one embodiment, a method for detecting congestive heart failure in an individual comprises directly or indirectly measuring a level of a caspase-3 proteolytic fragment in a plasma or serum sample from the individual, and comparing the level of the caspase-3 proteolytic fragment in the plasma or serum sample to a control level in a control sample, wherein the individual is in need of detection of congestive heart failure.

In another embodiment, a prognostic method for increased mortality and/or morbidity resulting from congestive heart failure in an individual comprises directly or indirectly measuring a level of a caspase-3 proteolytic fragment in a serum or plasma sample from the individual, comparing the level of the caspase-3 proteolytic fragment in the serum or plasma sample to a control level in a control sample, and predicting increased mortality and/or morbidity when the level of the caspase-3 proteolytic fragment in the serum or plasma sample is higher than that in healthy control subjects.

In yet another embodiment, a method for determining the success of a therapy for acute or stable congestive heart failure in an individual comprises directly or indirectly measuring a level of a caspase-3 proteolytic fragment in a serum or plasma sample from the individual, comparing the level of the caspase-3 proteolytic fragment in the serum or plasma sample to the level before such a therapy, and determining the success of the therapy for acute or stable congestive heart failure.

DETAILED DESCRIPTION

Apoptosis is both a physiologic and a pathophysiologic process. Recent evidence suggests a role for apoptosis in the progression of CHF. Caspase-3 is a downstream effector in the apoptosis cascade; in fact, cleaved caspase-3 is the final executioner of apoptotic cell death. During acute CHF, evidence exists that heart muscle apoptosis and/or apoptosis of congested engorged vasculature or skeletal muscle may become a source of cleaved caspase-3. However, it was not clear whether the cleaved caspase-3 can escape heart muscle cells or other tissues and become detectable in the circulation. In addition, it was not known whether the heart muscles and/or other tissues will have enough "apoptotic cell mass" to generate sufficient cleaved caspase-3 for detection during acute deteriorating heart failure (termed acute CHF). The inventors herein have unexpectedly discovered that cleaved caspase-3 products can be quantified in human serum and that it is elevated during acute CHF.

Caspase-3 (SEQ ID NO:1) is synthesized as an inactive proenzyme (32 kDa) that is processed in cells undergoing apoptosis by self-proteolysis and/or cleavage by another upstream protease. The processed form of caspase-3 consists of large (17 kDa; p17 fragment) (SEQ ID NO:2) and small (12 kDa; p12 fragment) (SEQ ID NO:3) subunits which associate to form an active enzyme. Disclosed herein are methods of detecting and/or prognosing congestive heart failure by detecting a proteolytic fragment of caspase-3 such as the p17 peptide or the p12 fragment.

In one embodiment, a method of detecting capase-3 fragment levels in a serum or plasma sample comprises directly or indirectly measuring a level of a caspase-3 proteolytic fragment in the serum or plasma sample. The method can further include comparing the level of the caspase-3 proteolytic fragment in the sample to a control level in a control sample. In one embodiment, the sample is from an individual who was not known to have congestive heart failure of any etiology, such as systolic or diastolic heart failure, ischemic or non-ischemic cardiomyopathy. In another embodiment, the sample is from an individual suspected of having congestive heart failure. In another embodiment, the individual has, or is suspected of having, HFpEF, a form of DHF. Indirect measuring includes, for example, performing an immunoassay with an antibody suitable for detection of a capase-3 proteolytic fragment.

In one embodiment, the control sample is from a normal population, or from the individual when the individual is not in an acute congestive heart failure state. In another embodiment, the congestive heart failure is acute congestive heart failure. In yet another embodiment, the control sample is from an individual who has chronic heart failure but is deemed to be stable and not in acute decompensated heart failure.

In another embodiment, the method further comprises diagnosing congestive heart failure when the level of the caspase-3 proteolytic fragment in the plasma or serum sample is substantially elevated compared to the control level, wherein the control level is measured from a serum sample when the individual is not in acute congestive heart failure.

In another embodiment, a method for detecting congestive heart failure in an individual comprises directly or indirectly measuring a level of a caspase-3 proteolytic fragment in a plasma or serum sample from the individual, and comparing the level of the caspase-3 proteolytic fragment in the plasma or serum sample to a control level in a control sample. In one embodiment, the congestive heart failure is acute congestive heart failure and optionally the control sample is from an individual with stable congestive heart failure. In one embodiment, the method further comprises diagnosing congestive heart failure when the level of the caspase-3 p17 proteolytic fragment in the serum or plasma sample is substantially elevated compared to the control level, wherein the control level is measured from a serum or plasma sample when the individual is not in acute congestive heart failure. The underlying form of congestive heart failure is, for example systolic or diastolic from any etiology, or ischemic or non-ischemic cardiomyopathy from any cause.

In another embodiment, a prognostic method for predicting increased mortality and/or morbidity resulting from congestive heart failure in an individual, comprises directly or indirectly measuring a level of a caspase-3 proteolytic fragment in a serum or plasma sample from the individual, comparing the level of the caspase-3 proteolytic fragment in the serum or plasma sample to a control level in a control sample, and predicting increased mortality and/or morbidity when the level of the caspase-3 proteolytic fragment in the serum sample is higher than that in healthy control subjects, such as when the level is in the top tercile or quartile or is increased by 20% or more compared to the control level in healthy subjects. Examples of morbidity include more severe heart failure symptoms, hospitalization for acute decompensated heart failure, and the need for intravenous diuretics, vasodilators, inotropic agents, placement of ventricular assist device, cardiac transplantation.

In yet another embodiment, a method for determining the success of a therapy for acute or stable congestive heart failure in an individual comprises directly or indirectly measuring a level of a caspase-3 proteolytic fragment in a serum or plasma sample from the individual, comparing the level of the caspase-3 proteolytic fragment in the serum sample to the level before such a therapy, and determining the success of the therapy for acute or stable congestive heart failure. The therapy is, for example, a medication or mechanical device. Exemplary mechanical devices include a biventricular pacing device, or a left ventricular or bi-ventricular assist device. In another embodiment, the method further comprises changing the therapy in response to an outcome of the therapy for the individual. In specific embodiments, changing the therapy includes increasing the dosage of current medication, initiating new medication, or initiating the mechanical device earlier in the therapy.

In one embodiment, the control sample is from a normal population, or from the individual when the individual is not in an acute congestive heart failure state. In another embodiment, the control sample is from the individual when the individual is in a stable congestive heart failure state.

Caspases are a family of cysteine acid proteases that are essential to the intracellular processes leading to apoptosis. Pro-apoptotic signals trigger the activation of the initiator caspases (such as caspase-8, -9, -10), which cleave and in turn activate the downstream effector caspases. Among the effector caspases, caspase-3 is considered to be the key executioner in the apoptotic pathway. It is activated by cleavage of its inactive zymogen into active p17 and p12 fragments. The cleaved p17 fragment can be detected with a commercial sandwich ELISA assay. The human caspase-3 has accession number NP_116786.

Caspase-3 (SEQ ID NO:1) has the sequence:
1   mentensvds  ksiknlepki  ihgsesmdsg  isldnsykmd ypemglciii nnknfhkstg
61  mlsrsgtdvd  aanlretfrn  lkyevrnknd  ltreeivelm rdvskedhsk rssfvcvlls
121 hgeegiifgt  ngpvdlkkit  nffrgdrcrs  ltgkpklfii qacrgteldc gietdsgvdd
181 dmachkipve  adflyaysta  pgyyswrnsk  dgswfiqslc amlkqyadkl efmhiltrvn
241 rkvatefesf  sfdatfhakk  qipcivsmlt  kelyfyh The p17 fragment is amino acids 29-175 (SEQ ID NO:2), and has the sequence:
sgisldnsyk mdypemglci iinnknfhks tgmtsrsgtd vdaanlretf rnlkyevrnk ndltreeive lmrdvskedh skrssfvcvl lshgeegiif gtngpvdlkk itnffrgdrc rsltgkpklf iiqacrgtel dcgietd The p12 fragment is amino acids 176-277 (SEQ ID NO: 3) and has the sequence:

sgvdd dmachkipve adflyaysta pgyyswrnsk dgswfiqslc amlkqyadkl efmhiltrvn rkvatefesf sfdatfhakk qipcivsmlt kelyfyh The term "level" relates to amount or concentration of a peptide or polypeptide in a patient or a sample taken from a patient. The term "measuring" accordingly relates to determining the amount or concentration, preferably semi-quantitatively or quantitatively, of the nucleic acid, peptide, polypeptide, or other substance of interest. Measuring can be done directly or indirectly. Indirect measuring includes measuring of cellular responses, bound ligands, labels, or enzymatic reaction products. In one embodiment, indirect measuring includes the use of an antibody.

The amount, level or presence of a caspase-3 proteolytic fragment is determined using any of a variety of techniques known to the skilled artisan such as, for example, a technique selected from the group consisting of, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), surface-enhanced laser desorption ionization mass spectrometry (SELDI-MS), biosensor technology, evanescent fiber-optics technology or protein chip technology.

In one embodiment the assay used to determine the amount or level of caspase-3 or a fragment thereof is a semi-quantitative assay. In another embodiment the assay used to determine the amount or level of caspase-3 or a fragment thereof is a quantitative assay. As will be apparent from the preceding description, such an assay may require the use of a suitable control, e.g., from a normal individual or matched normal control.

Standard solid-phase ELISA or FLISA formats are particularly useful in determining the concentration of a protein from a variety of samples.

Caspase-3 or a fragment thereof can be measured in the body fluid sample, e.g., serum or plasma, using assays that detect caspase-3 or a fragment thereof, for example, radio-isotopic immunoassays or non-isotopic immunoassays, e.g., fluorescent immunoassays, enzymatic immunoassays, such as an enzyme linked immunoassay (ELISA).

By way of example, other means for determining and measuring caspase-3 or a fragment thereof in a sample include affinity chromatography, ligand binding assays and lectin binding assays Immunoassays, especially non-radioisotopic immunoassays, are particularly suitable. Normal range and normal mean values can be determined for the assay being carried out based on normal (healthy) population samples, as is known and practiced in the art.

As used herein, the term antibody includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library. Antibodies useful as detector and capture antibodies may be prepared by standard techniques well known in the art.

Antibodies generated against caspase-3 or a fragment thereof, can be obtained by direct injection of an immunogenic caspase-3 preparation into an animal, or by administering all, or the caspase-3 p-17 polypeptides to an animal, preferably a nonhuman animal. For the preparation of monoclonal antibodies, a suitable technique which provides antibodies produced by continuous cell line cultures can be used. Examples include the hybridoma technique, the trioma technique, the human B-cell hybridoma technique, and the EBV-hybridoma technique to produce human monoclonal antibodies. Techniques described for the production of single chain antibodies can be adapted to produce single chain antibodies to caspase-3. Also, transgenic mice may be used to express humanized antibodies to immunogenic caspase-3 or a fragment thereof.

Methods for producing and screening for antibodies to caspase-3 or a fragment thereof using hybridoma technology are routine and well known in the art. In a nonlimiting example, mice can be immunized with an immunogen, caspase-3 or a fragment thereof, or with a cell expressing these polypeptides or peptides. Once an immune response is detected, e.g., antibodies specific for the antigen are detected in the sera of immunized mice, the spleen is harvested and splenocytes are isolated. The splenocytes are then fused by well-known techniques to any suitable myeloma cells available from the ATCC. Hybridomas are selected and cloned by limiting dilution techniques. The hybridoma clones are then assayed by methods known in the art to determine and select those cells that secrete antibodies capable of binding to caspase-3 or a fragment thereof. Ascites fluid, which generally contains high levels of antibodies, can be generated by injecting mice with positive hybridoma clones.

Caspase-3 or a fragment thereof comprising one or more immunogenic caspase-3 epitopes which elicit an antibody response can be introduced together with a carrier protein, such as an albumin, to a host animal (such as rabbit, mouse, rat, sheep, or goat). Alternatively, if the polypeptide is of sufficient length (e.g., at least about 25 amino acids), the polypeptide can be presented without a carrier. However, immunogenic epitopes comprising as few as 5 to 10 amino acids have been shown to be sufficient to raise antibodies capable of binding to, at the very least, linear epitopes in a denatured polypeptide (e.g., in Western blotting).

Caspase-3 or a fragment thereof can be used to induce antibodies according to methods well known in the art including, but not limited to, in vivo immunization, in vitro immunization, and phage display methods. If in vivo immunization is used, animals can be immunized with free peptide; however, the anti-peptide antibody titer may be boosted by coupling the peptide to a macromolecular carrier, such as keyhole limpet hemacyanin (KLH), or tetanus toxoid (TT). For instance, peptides containing cysteine residues can be coupled to a carrier using a linker such as maleimidobenzoyl-N-hydroxysuccinimide ester (MBS), while other peptides may be coupled to carriers using a more general linking agent, such as glutaraldehyde.

Antibodies specific for caspase-3 or a fragment thereof are produced by methods known in the art for the synthesis of antibodies, in particular, by chemical synthesis, by intracellular immunization (i.e., intrabody technology), or by recombinant expression techniques. Methods of producing antibodies include, but are not limited to, hybridoma technology, EBV transformation, as well as through the use recombinant DNA technology. Recombinant expression of an antibody, or a fragment, derivative, variant or analog thereof, (e.g., a heavy or light chain of an anti-caspase-3 antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule can be produced by recombinant DNA technology using techniques well known in the art. In vitro recombinant DNA techniques, synthetic techniques, and in vivo genetic recombination methods, which are well known to those skilled in the art, can be used to construct expression vectors containing antibody coding sequences and appropriate transcriptional and translational control signals. Such vectors can include the nucleotide sequence encoding the constant region of the antibody molecule and the variable region of the antibody cloned into such a vector for expression of the entire heavy or light chain.

The expression vector is then introduced into a host cell by conventional techniques and the transfected cells are cultured by conventional techniques to produce an anti-capase-3 antibody. A variety of host expression vector systems can be utilized to express the antibody molecules. Such expression systems represent vehicles by which the coding sequences of interest can be expressed, their encoded products produced and subsequently purified. These systems also represent cells which can, when transformed or transfected with the appropriate nucleotide coding sequences, express an antibody molecule of the invention in situ. Cell expression systems include, but are not limited, to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces* or *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus (CaMV) or tobacco mosaic virus (TMV)), transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Specifically, bacterial cells such as *E. coli*, and more specifically, eukaryotic cells, especially for the expression of whole recombinant antibody molecules, are used for the expression of a recombinant antibody molecule. For example, mammalian cells such as Chinese hamster ovary (CHO) cells, in conjunction with a vector such as the major intermediate early gene promoter element from human cytomegalovirus, is an effective expression system for antibody production.

Once an anti-caspase-3 antibody has been produced by an animal, chemically synthesized, or recombinantly expressed, it can be purified by methods known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins.

In one embodiment, an ELISA assay initially involves preparing an antibody specific to caspase-3 or a fragment thereof, preferably a monoclonal antibody. In addition, a reporter antibody is used. In some ELISA protocols, the reporter antibody recognizes and binds to the caspase-3 specific monoclonal antibody. To the reporter antibody is attached a detectable reagent such as a radioactive isotope, a fluorescent moiety, a chemiluminescent moiety, or, in an ELISA, an enzyme, such as horseradish peroxidase or alkaline phosphatase.

As is appreciated by those skilled in the art, ELISAs can be performed in a number of assay formats. In one ELISA format, a host sample, e.g., a patient body fluid sample, is incubated on a solid support, e.g., the wells of a microtiter plate, or a polystyrene dish, to which the proteins in the sample can bind. Any free protein binding sites on the dish are then blocked by incubating with a non-specific protein such as bovine serum albumin. The monoclonal antibody is then added to the solid support, e.g., the wells or the dish, and allowed to incubate. During the incubation time, the monoclonal antibodies attach to any caspase-3 polypeptides that have attached to the polystyrene dish.

Unbound monoclonal antibody is washed away using an appropriate buffer solution. The reporter antibody, e.g., linked to horseradish peroxidase, is added to the support, thereby resulting in the binding of the reporter antibody to any monoclonal antibody which has bound to caspase-3 or a fragment thereof present in the sample. Unattached reporter antibody is then washed away. Peroxidase substrate is added to the support and the amount of color developed in a given time period provides a measurement of the amount of caspase-3 or a fragment thereof that is present in a given volume of patient sample when compared to a standard curve.

In another ELISA format, antibody specific for a particular analyte is attached to the solid support, i.e., the wells of a microtiter plate or a polystyrene dish, and a sample containing analyte is added to the substrate. Detectable reporter antibodies, which bind to the analyte that has bound to the capture antibodies on the support, are then added, after the appropriate incubations and washings, and analyte-antibody complexes are detected and quantified.

In one embodiment, the ELISA assay is a sandwich type ELISA immunoassay typically performed using microtiter plates. A capture antibody, that can be polyclonal or monoclonal, preferably a monoclonal antibody, that specifically recognizes an epitope in the extracellular portion caspase-3 or a fragment thereof is used, along with a labeled detector antibody, e.g., an alkaline phosphatase-labeled antibody, or a horse radish peroxidase-labeled antibody, preferably a monoclonal antibody. The detector antibody also specifically recognizes an epitope on the extracellular protein domain of caspase-3 or a fragment thereof. Preferably, the capture antibody does not inhibit binding to caspase-3 or a fragment thereof. The production of both polyclonal and monoclonal antibodies, particularly monoclonal antibodies that are specific for caspase-3 or a fragment thereof, is performed using techniques known in the art.

In a particular embodiment, a capture anti-caspase-3 antibody of the assay method, is immobilized on the interior surface of the wells of the microtiter plate. To perform the assay, an appropriate volume of sample is incubated in the wells to allow binding of the antigen by the capture antibody. The immobilized antigen is then exposed to the labeled detector antibody. Addition of substrate to the wells, if the detectable label is alkaline phosphatase, for example, allows the catalysis of a chromogen, i.e., para-nitrophenylphosphate (pNPP), if the label is alkaline phosphatase, into a colored product. The intensity of the colored product is proportional to the amount of caspase-3 that is bound to the microtiter plate.

Standards are used to allow accurate quantitative determinations of caspase-3 or a fragment thereof in the samples undergoing analysis. A microtiter plate reader simultaneously measures the absorbance of the colored product in the standard and the sample wells. Correlating the absorbance values of samples with the standards run in parallel in the assay allows the determination of the levels of caspase-3 or a fragment thereof in the sample. Samples are assigned a quantitative value of caspase-3 or a fragment thereof in nanograms per milliliter (ng/ml) of serum, plasma, other body fluid, or cell culture fluid.

For ease and simplicity of detection, and its quantitative nature, an exemplary assay is the sandwich or double antibody assay of which a number of variations exist. In one embodiment of a sandwich assay, unlabeled antibody is immobilized on a solid phase, e.g., a microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

Alternatively, the amount of caspase-3 or a fragment thereof is detected using a radioimmunoassay (RIA). The basic principle of the assay is the use of a radiolabeled antibody or antigen to detect antibody-antigen interactions. An antibody or ligand that specifically binds to a protein is bound to a solid support and a sample brought into direct contact with said antibody. To detect the level of bound antigen, an isolated and/or recombinant form of the antigen is radiolabeled and brought into contact with the same antibody. Following washing, the level of bound radioactivity is detected. As any antigen in the biological sample inhibits binding of the radiolabeled antigen the level of radioactivity detected is inversely proportional to the level of antigen in the sample. Such an assay may be quantitated by using a standard curve using increasing known concentrations of the isolated antigen.

In another embodiment, Western blotting is used to determine the level of caspase-3 or a fragment thereof in a sample. In such an assay protein from a sample is separated using sodium doedecyl sulphate polyacrylamide gel electrophoresis (SDS-PAGE) using techniques known in the art. Separated proteins are then transferred to a solid support, such as, for example, a membrane (e.g., a PVDF membrane), using, for example, electrotransfer. This membrane is then blocked and probed with a labeled antibody or ligand that specifically binds to caspase-3 or a fragment thereof. Alternatively, a labeled secondary, or even tertiary, antibody or ligand is used to detect the binding of a specific primary antibody. The level of label is then determined using an assay appropriate for the label used.

In other embodiments, the detection of the level of caspase-3 or a fragment thereof is done by a method such as, for example, mass spectrometry, matrix-assisted laser desorption/ionization time of flight (MALDI-TOF), electrospray ionisation (ESI), protein chip, biosensor technology, or fluorescence resonance energy transfer.

Biosensor devices generally employ an electrode surface in combination with current or impedance measuring elements to be integrated into a device in combination with the assay substrate (such as that described in U.S. Pat. No. 5,567,301). An antibody/ligand that specifically binds to a protein of interest is preferably incorporated onto the surface of a biosensor device and a biological sample contacted to said device. A change in the detected current or impedance by the biosensor device indicates protein binding to said antibody. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nanoscales. Furthermore, such systems are conveniently adapted to incorporate several detection reagents, allowing for multiplexing of diagnostic reagents in a single biosensor unit. This permits the simultaneous detection of several proteins or peptides in a small amount of body fluid.

The data presented herein clearly show that a cleaved caspase-3 product, the caspase-3 p17 fragment, is detectable in human circulation. The caspase-3 p17 level is increased by nearly 100 percent in patients with acute CHF whether the underlying form of heart failure is systolic or diastolic. Thus, the level of caspase-3 proteolytic fragment can be used as a novel marker for acute systolic or diastolic form of CHF whether the etiology of heart failure is ischemic or non-ischemic cardiomyopathy.

Elevated levels of caspase-3 proteolytic fragments in heart failure patients indicate a greater level of apoptosis and can be used to predict the adverse course of heart failure. The caspase-3 proteolytic fragment levels serve as a prognostic indicator for increased mortality and/or morbidity. In one embodiment, an individual's level of caspase-3 proteolytic fragments is elevated when the patient is in acute CHF compared to the control level when the patient is not in acute CHF, such as when the patient is in stable CHF. Congestive heart failure is diagnosed when the level of a caspase-3 proteolytic fragment in the serum sample is substantially elevated compared to a control level, wherein the control level is from a patient sample when the patient is not in acute CHF, for example, when the patient has stable CHF. Alternatively, congestive heart failure is diagnosed when the level of a caspase-3 proteolytic fragment in the serum sample is substantially elevated compared to a control level, wherein the control level is from a normal population, that is, a standardized population. By substantially elevated, it is meant that the level is increased by 20% or more, specifically 50% or more, and more specifically 100% or more.

CHF occurs when heart function becomes insufficient to pump blood via the circulatory system to meet the needs of the vital systems and tissues of the body. The inability of the heart to pump sufficiently is correlated to the measured ejection fraction, which is the percent of the blood pumped out during each heartbeat. This inability can be caused by failure of one or more sides of the heart, typically the left but also the right side; such failure can result from systolic or diastolic dysfunction, and result in a backup of fluid and accumulation of fluid in the lungs. In diastolic heart failure, the systolic function as measured by left ventricular ejection fraction is normal. However, there is backward failure that causes vascular and pulmonary congestion. Although less common, right-sided heart failure will result in fluid backup that manifests in a swelling of the veins and surrounding body tissues, inadequate tissue perfusion, fatigue and poor exercise tolerance. In addition, heart failure can result from long-standing hypertension, valvular disease, transient ischemia, myocarditis, infiltrative disorders or congenital conditions such as hypertrophic cardiomyopathy.

Compared to acute CHF, chronic CHF is a longer term, slowly progressive degenerative disease. Over years, chronic CHF leads to cardiac insufficiency. Chronic CHF is clinically categorized by the patient's ability to exercise or perform normal activities of daily living. Chronic CHF patients are usually managed on an outpatient basis, typically with drugs. A CHF subject with chronic heart failure can be either stable or decompensated.

Chronic CHF patients may experience an abrupt, severe deterioration in heart function, termed acute CHF, resulting in the inability of the heart to maintain sufficient blood flow and pressure to keep vital organs of the body alive. These acute CHF deteriorations can occur when extra stress (such as an infection or excessive fluid overload) significantly increases the workload on the heart in a stable CHF patient. In contrast to the stepwise downward progression of chronic CHF, a patient suffering acute CHF may deteriorate from even the earliest stages of CHF to severe hemodynamic collapse. In addition, Acute CHF can occur within hours or days following an Acute Myocardial Infarction (AMI), which is a sudden, irreversible injury to the heart muscle, commonly referred to as a heart attack The underlying reasons for CHF are multiple. Thinning and weakening of the ventricle walls leads to dilation and a loss of pumping ability (systolic dysfunction). Alternatively, loss of elasticity results in a stiffening, which may result in a diminished volume of the heart's chambers and decreased cardiac output (diastolic dysfunction) and cardiac output. Additionally, abnormalities in the functioning of the heart's valves such as stenosis can lead to insufficient cardiac output, for which the body attempts to compensate by causing the heart to increase its heart rate, hypertrophy and/or dilate. The compensation mechanisms utilized by the body may lead to architectural changes in the form of remodeling (especially after MI) or adaptation of the heart muscle, ultimately leading to irrevocable loss of function. Related causes of cardiac failure may be one or more conditions such as coronary artery disease causing chronic low-coronary flow, ischemic heart damage, e.g., damage resulting from a heart attack, uncontrolled hypertension, the direct and/or indirect effects of diabetes on the heart, valvular heart disease, cardiomyopathy, autoimmune response, disease and abuse by external agents such as alcohol, tobacco, anabolic steroids, and the like.

Initial evidence for a diagnosis of CHF requires a history and a physical examination during which the condition is often characterized by various signs and symptoms of intravascular and interstitial volume overload, including shortness of breath, irregular heart rate, abnormal heart rate and signs of edema. To determine the severity and prognosis of CHF and to more clearly characterize a particular patient's condition, further diagnostic tests are usually needed. Further, a test that will gauge the success of CHF therapy is lacking, whether the therapy consists of medications or mechanical device such as bi-ventricular pacing or left ventricular assist device. A simple test that will predict mortality and morbidity of CHF patients is also lacking.

For the purposes of better understanding DHF, defining a pure population of patients with DHF is difficult since the syndrome can exist with diabetes, coronary disease, connective diseases, obesity and infiltrative disease. However, a stereotypical patient would be an older hypertensive woman whose left ventricular mass may is increased with no increase in end diastolic volume, whose left atrium is slightly dilated, and who may come to attention because of congestive symptoms precipitated by atrial fibrillation. The incidence of prior myocardial infarction is lower. While length of hospitalization is similar, mortality in hospital and over five years is slightly lower.

Heart failure with preserved ejection fraction (HFpEF), is a form of DHF, is defined by the European Society of Cardiology. Accordingly, a patient should have typical symptoms of congestive heart failure with shortness of breath and edema, an ejection fraction >50%, an end diastolic volume index <97 ml/m$^2$ and evidence of diastolic dysfunction with a PCWP >12 or LVEDP >16 mmHg, a tissue Doppler E/E' ratio >15, or a BNP level >200 pg/ml.

The disclosure is further illustrated by the following non-limiting examples.

EXAMPLES

Methods:
Identification of Patients:

A sample of 59 patients diagnosed with congestive HF were enrolled from the University of Connecticut Health Center ("UCHC") between January 2006 and December 2008. Subjects were eligible if they were being treated for HF as determined by symptoms (e.g., fatigue, dyspnea on exertion, poor exercise tolerance, orthopnea, PND, abdominal swelling, lower extremity edema), signs (e.g., increased work of breathing, jugular venous distention, rales, present third heart sound, hepatomegaly, ascites, lower extremity edema), imaging (e.g. reduced ejection fraction by 2-dimensional echocardiography or radionuclide scanning, cardiomegaly and pulmonary edema on chest x-ray), catheterization (e.g. reduced ejection fraction, elevated left ventricular end-diastolic pressure), and/or laboratory values (e.g. elevated BNP). Subjects were excluded if they were unable to give consent or had surgery in the 3 months prior to enrollment (not including cardiac catheterization). Institutional Review Board approval was obtained for the study and written informed consent was obtained from all participants.

Subjects were designated as "stable" if the treatment provider felt that symptoms were maximally reduced with optimal medical management. Subjects were designated as "decompensated" if they presented with new onset CHF, new signs/symptoms in a patient known to have a history of CHF, or advancing severity of baseline symptoms.

Cleaved Caspase-3 Assay:

Subjects underwent venipuncture to obtain a single gold-top (plasma) tube of blood. Samples were centrifuged for 15 minutes at 4° C. and the plasma was stored at −80° C. The PathScan™ Cleaved Caspase-3 (Asp175) Sandwich ELISA Kit from Cell Signaling Technology® was used to isolate the p17 fragment of caspase-3. Briefly, serum samples were thawed on ice and diluted to 1:1 (sample:diluent) using supplied diluent and plated into wells coated with caspase-3 antibody, which binds both full length caspase-3 and the p17 fragment. Plates were incubated overnight at 4° C., washed, and incubated with cleaved caspase-3 (Asp175) antibody for 60 minutes at 37° C., which recognizes only the cleaved p17 fragment of caspase-3. Samples were then incubated with horseradish peroxidase (HRP)-linked secondary antibody for 30 minutes at 37° C. The chromogenic substrate 3,3 ',5,5'-tetramethylbenzidine (TMB) was used for spectrophotometric analysis at 450 nm ($OD_{450}$). All samples were run in triplet for 5-, 10- and 20-minute incubation periods with TMB at 25° C.

Patient Characteristics and demographics are summarized in Table 1.

TABLE 1

Baseline Characteristics of Study Group (N = 59)*

| Demographic and Clinical Features | Mean ± SD or Number (%) | |
|---|---|---|
| | Stable | Decompensated |
| Age | 75.1 ± 13.5 | |
| Race, White/Non-White | 50 (85)/9 (15) | |
| Gender, Male/Female | 40 (68)/19 (32) | |

TABLE 1-continued

Baseline Characteristics of Study Group (N = 59)*

| Demographic and Clinical Features | Mean ± SD or Number (%) | |
|---|---|---|
| | Stable | Decompensated |
| Etiology of HF | | |
| Ischemic | | 22 (37) |
| Non-Ischemic | | 11 (19) |
| Combined | | 3 (5) |
| Preserved LV Function | | 23 (39) |
| Risk Factors: | | |
| Tobacco, Current/Former/Never | | 3 (5)/29 (49)/27 (46) |
| History of Diabetes | | 28 (48) |
| History of CAD | | 38 (64) |
| History of HTN | | 40 (68) |
| History of Dyslipidemia | | 44 (75) |
| History of A-Fib | | 30 (51) |
| History of PVD | | 10 (17) |
| History of CVA/TIA | | 7 (12) |
| Reperfusion History: | | |
| Status post-CABG | | 14 (24) |
| Status post-PCI | | 20 (34) |
| Devices: | | |
| PM, None/Single Chamber/Dual Chamber/Bi-ventricular | | 43 (73)/1 (2)/6 (10)/9 (15) |
| Status-post ICD | | 17 (29) |
| Catheterization Data: | | |
| CAD, None/One vessel/Two Vessel/Three Vessel (N = 28) | | 4 (14)/9 (32)/2 (7)/13 (47) |
| LVEDP (N = 18) | | 19.3 ± 8.4 |
| NYHA symptom class (N = 58): | | |
| I | 2 (3) | 0 (0) |
| II | 24 (41) | 4 (7) |
| III | 31 (54) | 35 (60) |
| IV | 1 (2) | 19 (33) |
| Vitals: | | |
| Blood Pressure - mmHg | 116.9 ± 18.4/ 65.7 ± 12.3 | 131.0 ± 28.4/ 72.4 ± 17.5 |
| HR - beat/min | 71.8 ± 11.0 | 79.7 ± 16.1 |
| Weight - kg | 192.7 ± 52.0 | 203.7 ± 61.9 |
| Laboratory measurements: | | |
| BNP - pg/mL (N = 41|N = 59) | 732.7 ± 665.8 | 1111.2 ± 1041.8 |
| Creatinine - mg/dL (N = 46|N = 59) | 1.7 ± 0.7 | 2.4 ± 3.4 |
| eGFR - mL/min (N = 52|N = 59) | 47.4 ± 28.5 | 46.6 ± 23.4 |
| Hemoglobin - mg/dL (N = 47|N = 59) | 11.4 ± 2.1 | 11.9 ± 2.0 |
| WBC count - K/uL (N = 41|N = 59) | 7.8 ± 2.9 | 8.1 ± 3.0 |
| Cardiac Enzymes (N = 51): | | |
| Creatinine Kinase (CK) - U/L | | 334.0 ± 1250.2 |
| CK-MB fraction - U/L | | 7.4 ± 14.1 |
| Troponin I - ng/mL | | 1.2 ± 6.1 |
| Medications: | | |
| Beta-blocker | 40 (68) | 33 (56) |
| Aspirin | 33 (56) | 28 (48) |
| ACE-i | 26 (44) | 21 (36) |
| ARB | 13 (22) | 11 (19) |
| Nitrate | 8 (14) | 6 (10) |
| Statin | 36 (61) | 36 (61) |
| Loop Diuretic | 48 (81) | 47 (80) |
| Aldosterone Antagonist | 19 (32) | 13 (22) |
| Calcium Channel Blocker | 8 (14) | 7 (12) |
| Digoxin | 13 (22) | 12 (20) |
| Epogen | 3 (5) | 3 (5) |
| Ejection Fraction - % (N = 18|N = 58) | 32.9 ± 16.7 | 35.7 ± 19.7 |
| Echocardiographic Data: (N = 18|N = 58) | | |
| Severe Valvular Disease | 7 (39) | 15 (26) |
| LVH | 7 (39) | 23 (40) |
| Elevated estimated peak pulmonary artery pressures - mmHg (N = 10|N = 32) | 53.1 ± 20.0 | 51.4 ± 16.5 |
| Caspases levels (N = 59|N = 59) | 0.07 ± 0.06 | 0.09 ± 0.07 |

*Laboratory, imaging, and catheterization data not available for all subjects.

The clinical characteristics and demographics of patients at the time of enrollment were determined from medical records of patients. Etiology of HF was determined to be ischemic by evidence of significant coronary disease in the setting of reduced ejection fraction (EF). "Non-ischemic cardiomyopathy" was suggested by a reduced EF in the absence of significant epicardial coronary artery disease. Finally all patients with EF>50% were considered to have heart failure with "preserved systolic function", which is also known as diastolic heart failure.

Symptoms were classified according to fulfillment of New York Heart Association (NYHA) functional classes I-IV. Relevant cardiac medications were indicated. Various laboratory values were recorded for patients hospitalized with decompensated HF and when they are stable.

Cardiac Catheterization and Echocardiography were performed at UCHC using current established standards.

Statistical Analyses:

Paired t-test to ensure normality of distribution as well as the non-parametric Wilcoxon Signed Rank test for paired samples. Comparison of continuous variables was assessed using independent unpaired t-test. Categorical variable was compared using 2×2 contingency table and Fisher's Exact Test. A p value of less than 0.05 was considered significant. All P-values reported are two-sided. Statistical analyses were performed with SPSS version 15.0 (SPSS Inc, Chicago, Ill.).

Example 1

Assay Development

Figure 1:
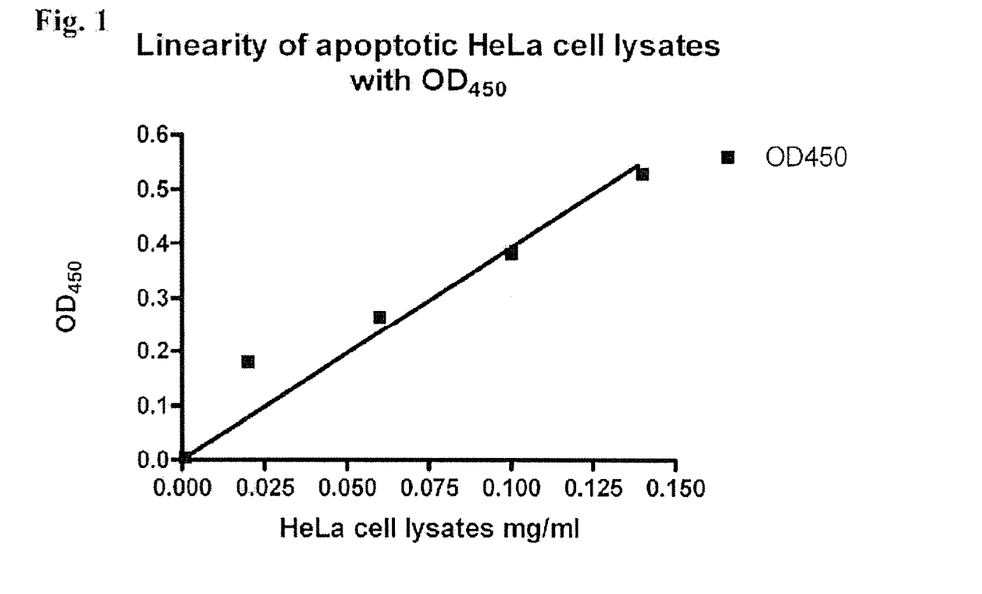
FIG. 1. Linearity of the assay for caspase-3 p17 peptide using apoptotic HeLA cell lysates. As a positive control, apoptosis of HeLa cell cultures (90% confluent) was induced by exposure to staurosporine (1 µM) for three hours at 37° C. $OD_{450}$ represented the amount of p17 peptide. Cell lysates were run at various concentrations using identical ELISA conditions and served as a positive control for caspase-3 p17 peptide.

We have developed an assay to quantify the level of the p17 peptide of caspase-3 in human serum based on an Enzyme-Linked Immunosorbant Antibody (ELISA) method. The level of caspase-3 P17 level varied directly with the amount of serum in heart failure patients. As a positive control, apoptosis of HeLa cell cultures (90% confluent) was induced by exposure to staurosporine (1 μM) for three hours at 37° C. $OD_{450}$ represented the amount of p17 peptide. Cell lysates were run at various concentrations using identical ELISA conditions and served as a positive control for caspase-3 p17 peptide. The serum caspase-3 P17 level was in the linear range of the assay relating the level of this P17 peptide to the amount of apoptotic HeLa cell lysates, which served as a positive control (FIG. 1). Linearity of the assay for caspase-3 p17 peptide using apoptotic HeLA cell lysates was demonstrated.

Example 2

Level of Caspase-3 P17 Fragment in Patients

Figure 2:
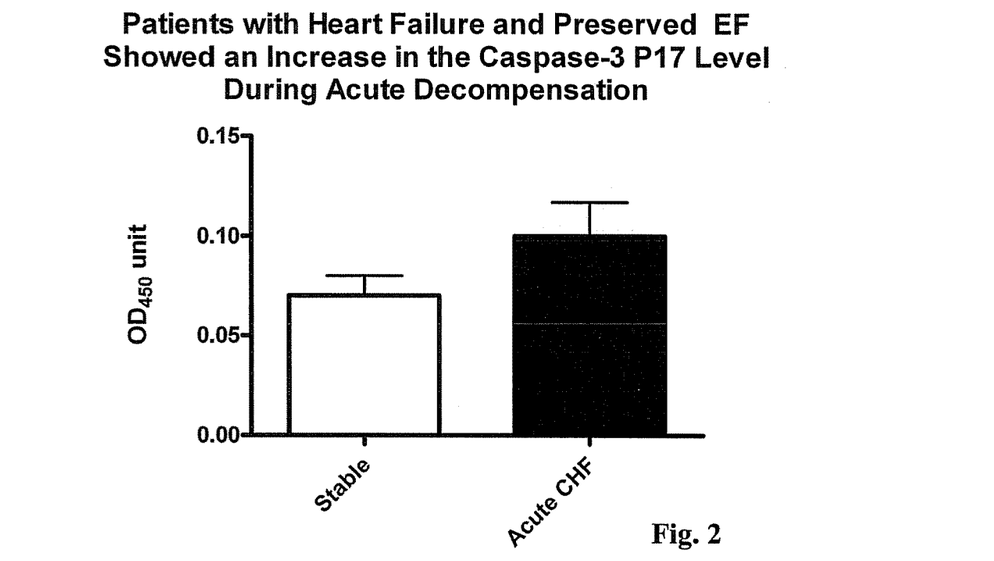
FIG. 2. The p17 peptide was elevated in patients with heart failure with preserved ejection fraction (HFpEF) during acute decompensation. Serum samples from 18 patients with HFpEF were collected during acute decompensation and under stable conditions. An assay for the level of caspase-3p17 peptide was carried out using an ELISA. P17 peptide was significantly elevated during acute decompensation as compared to that determined under stable clinical conditions when heart failure was not present (Wilcoxon signed rank test, $p<0.0001$). The levels for each subject under the acute and stable conditions were determined at the same time during the same assay run.
Figure 3:
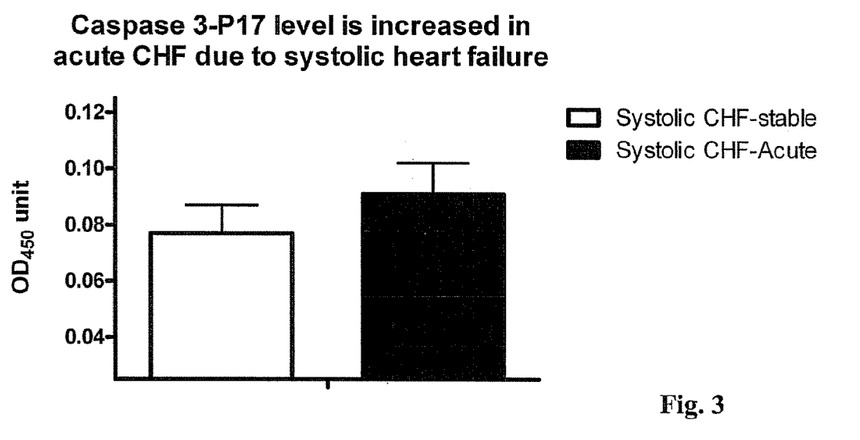
FIG. 3 shows a significant increase in the circulating level of caspase-3 P17 fragment in acute CHF due to systolic heart failure.

Patients with HFpEF showed a significant increase in the circulating level of caspase-3 P17 fragment during acute decompensation (FIG. 2). Caspase-3 P17 level increased from a basal $OD_{450}$ level of 0.07±0.001 to a level of 0.10±0.017 during acutely decompensated heart failure, representing a 40±4.5% increase (±S.E.M, n=23 patients, P<0.0001, Wicoxon signed rank test). These data supported the concept that apoptosis was increased during the transition of stable heart failure to acute decompensation in HFpEF. In those with systolic heart failure, caspase-3 P17 level increased from a basal $OD_{450}$ level of 0.077±0.01 to a level of 0.091±0.011 during acutely decompensated heart failure, representing a 30±10% increase (±S.E.M, n=36 patients, P<0.0001, Wicoxon signed rank test) (FIG. 3). These data supported the concept that apoptosis was increased during the transition of stable heart failure to acute decompensation in systolic heart failure patients.

Figure 4:
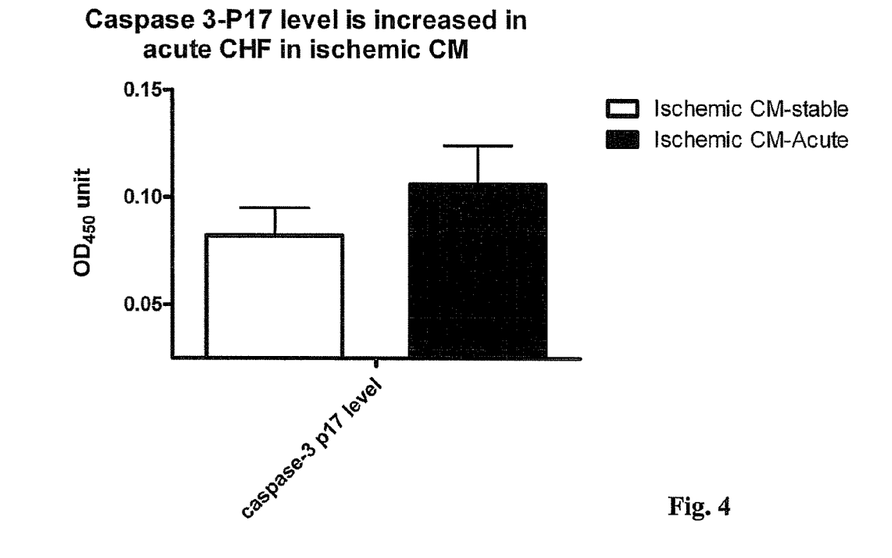
FIG. 4 shows a significant increase in the circulating level of caspase-3 P17 fragment in acute CHF in ischemic cardiomyopathy.
Figure 5:
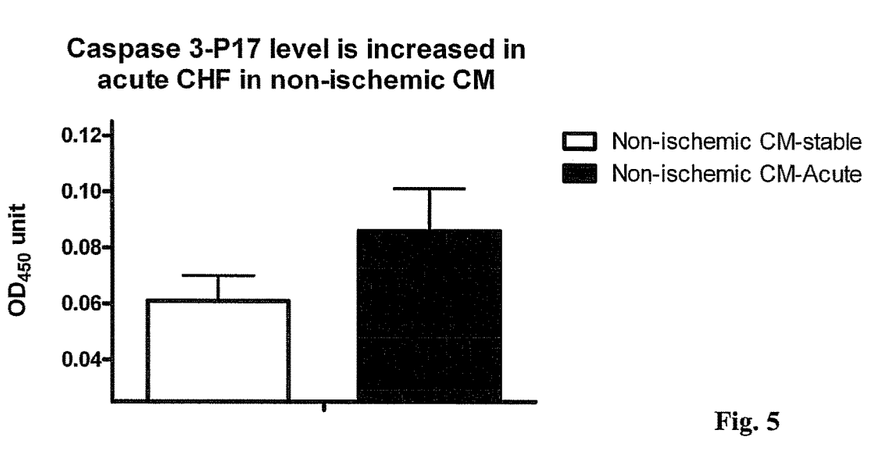
FIG. 5 shows a significant increase in the circulating level of caspase-3 P17 fragment in acute CHF in non-ischemic cardiomyopathy.

The increase in p17 level during acute HF was also significant whether the etiology of HF was ischemic (P=0.009, S.E.M., n=21) (FIG. 4) or non-ischemic (p=0.027, n=9) (FIG. 5). In the entire cohort of HF patients, those who presented with NYHA class IV symptoms during acute decompensation had higher p17 levels during both acute and stable conditions (P<0.05). The p17 level during acute decompensation correlated with the troponin-I level (Spearman r=0.35, p=0.023). The stable and decompensated p17 levels in systolic HF were similar to the respective stable and decompensated levels in diastolic HF (P>0.1). Likewise, the respective stable and decompensated p17 levels were also similar in the ischemic HF vs. non-ischemic HF comparison (P>0.1).

Example 3

Preparation of Samples for Mass Spectrometry

Prior to performing mass spectrometry on serum samples, it is advantageous to remove highly abundant, high molecular weight proteins such as serum albumin and immunoglobulins so that low molecular markers such as caspase-3 protease fragments can be determined Dye ligands and protein A and G columns can be used to remove serum albumin and immunoglobulins from serum, allowing detection of low concentration biomarkers. Dialysis and molecular-weight cutoff filters may also be employed. Acetonitrile precipitation is another method to remove serum albumin and immunoglobulins from serum because acetonitrile not only denatures proteins allowing but also dissociates smaller proteins from these carrier proteins making them available for detection. Two-dimensional gel separation followed by mass spectrometry analysis may also be employed.

Example 4

Mass Spectrometry of Caspase Proteolytic Fragments

Mass spectrometry provides a means to specifically detect different forms of a protein in a sample. In mass spectrometry analytes are separated by mass and can be distinguished based on their mass signature. Thus, fragments of a protein such as caspase-3 can be distinguished from a full-length protein. Furthermore, the mass also can indicate the particular location of the fragment within the protein.

In one embodiment, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

Biospecific adsorbents include those molecules that bind a target analyte with an affinity of at least $10^{-9}M$, $10^{-10}M$, $10^{-11}M$ or $10^{-12}$ M. Biospecific capture reagents include antibodies, binding fragments of antibodies and other molecule that specifically binds to a caspase-3 proteolytic fragment. Depending on the intended use, they also may include receptors and other proteins that specifically bind another biomolecule. In a SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

The biological sample to be tested as used herein is a plasma or serum sample. The sample to be tested is contacted with an affinity capture probe comprising an anti-caspase-3 antibody. The probe is washed with a buffer that will retain caspsase-3 proteolytic fragments and anti-caspase-3 antibodies while washing away unbound molecules. The analytes are detected by laser desorption/ionization mass spectrometry.

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. Analysis involves the identification of peaks in the spectrum that represent signal from an analyte. Peak selection can be done visually, but software is available that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Example 5

LC-MS/MS Analysis

Immunoaffinity caspase-3 proteolytic fragment are loaded onto a peptide trapping column before being resolved with a C18 analytical column, ionized using microelectrospray ionization, and analyzed using multiple reaction monitoring (MRM). Fragment ion spectra are collected in the linear ion trap of the mass spectrometer simultaneously with the collection of MRM data.

Caspase-3 proteolytic fragments, specifically the caspase-3 P17 fragment, is a new circulating biomarker for HFpEF. This marker may correlate with BNP, with markers of myocardial injury such as troponin or creatine kinase MB, with NYHA functional class, or with creatinine clearance. In the present clinical investigation of caspase-3 p17, BNP was also more elevated during acute decompensation in the patients with HFpEF, further supporting caspase-3 p17 as a marker for acute diastolic heart failure. The caspase-3 p17 level is elevated during acute decompensation in patients with either systolic or diastolic HF. It is also elevated whether the HF etiology is ischemic or non-ischemic. An elevated p17 level is associated with NYHA class IV symptoms during acute decompensation. Circulating caspase-3 proteolytic fragment levels may be a promising new biomarker for all forms of HF.

The caspase-3 p17 peptide is unlike the other biomarkers for heart failure as it is linked to apoptotic cell death, and not to inflammation, necrotic cell death, stretch or stress, oxidized stress or extracellular matrix remodeling. It is not a neurohormone like angiotensin II, endothelin or catecholamine. Thus, the link to a different pathophysiology distinguishes this peptide as a biomarker for heart failure. That its level is elevated during acute decompensation in patients with HFpEF implies a link between apoptosis and acute diastolic heart failure and raises the possibility that it may be a useful biomarker for this group of patients.

The terms "a" and "an" herein do not denote a limitation of quantity, but rather denote the presence of at least one of the referenced item.

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

---

The invention claimed is:

1. A method for determining the success of a therapy for acute or stable congestive heart failure in an individual, comprising
   directly or indirectly measuring a level of a caspase-3 proteolytic fragment in a serum or plasma sample from the individual, wherein the caspase-3 proteolytic fragment is the p17 or the p12 fragment,
   comparing the level of the caspase-3 proteolytic fragment in the serum or plasma sample to the level before such a therapy, and
   determining the success of the therapy for acute or stable congestive heart failure.

2. The method of claim 1, wherein the therapy is a medication or mechanical device.

3. The method of claim 2, wherein the mechanical device is abiventricular pacing device, or a left ventricular or bi-ventricular assist device.

4. The method of claim 1, further comprising changing the therapy in response to an outcome of the therapy for the individual.

5. The method of claim 4, wherein changing the therapy in response to the outcome comprises increasing the dosage of current medication, initiating new medication, or initiating the mechanical device earlier in the therapy.

* * * * *